United States Patent
Zilioli et al.

(10) Patent No.: US 7,485,175 B2
(45) Date of Patent: Feb. 3, 2009

(54) DEVICE FOR POSITIONING AND HOLDING A LENGTH OF GAS CHROMATOGRAPHIC COLUMN

(75) Inventors: Giacinto Zilioli, Rodano (IT); Daniela Cavagnino, Rodano (IT); Tiziano Bosaglia, Rodano (IT)

(73) Assignee: Thermo Electron S.p.A., Rodano (MI) (IT)

( * ) Notice: Subject to any disclaimer, the term of this patent is extended or adjusted under 35 U.S.C. 154(b) by 236 days.

(21) Appl. No.: 11/435,279

(22) Filed: May 17, 2006

(65) Prior Publication Data

US 2006/0266218 A1 Nov. 30, 2006

(30) Foreign Application Priority Data

May 26, 2005 (IT) .......................... MI2005A0980

(51) Int. Cl.
*B01D 53/02* (2006.01)
*B01L 9/00* (2006.01)

(52) U.S. Cl. ............................... 96/101; 95/87; 422/104

(58) Field of Classification Search .................. 96/101, 96/104, 106; 95/82, 86, 87; 73/23.35, 23.39; 210/198.2, 656; 422/104

See application file for complete search history.

(56) References Cited

U.S. PATENT DOCUMENTS 6,126,122 A 10/2000 Ismert et al.
6,190,613 B1 * 2/2001 Watanabe et al. ............. 422/99
6,446,915 B1 9/2002 Ismert
6,838,288 B2 * 1/2005 Beens ......................... 436/161
7,258,726 B2 * 8/2007 Ledford, Jr. .................... 95/82
2003/0100124 A1 5/2003 Beens
2005/0139076 A1 6/2005 Ledford, Jr.
2006/0008390 A1 * 1/2006 Prentice et al. ............. 422/104

FOREIGN PATENT DOCUMENTS

WO WO 02/39106 A 5/2002
WO WO 03/082427 A 10/2003
WO WO 03/089141 A 10/2003

OTHER PUBLICATIONS

Kristenson et al, "Evaluation of modulators and electron-capture detectors for comprehensive two-dimensional GC of . . . ", Journal of Chromatography, Elsevier Science Publishers B.V. Amsterdam, NL, vol. 1019, No. 1-2, Nov. 26, 2003, pp. 65-77, XP004469917.

* cited by examiner

*Primary Examiner*—Duane S Smith
*Assistant Examiner*—Robert A Clemente
(74) *Attorney, Agent, or Firm*—Nixon & Vanderhye P.C.

(57) ABSTRACT

The invention relates to a device for positioning and holding one or more chromatographic column lengths being subjected to one or more jets of fluid to change the temperature, especially in a modulator for GC×GC. The device comprises one or more V-shaped seats in which the column is housed, and pushed within the groove.

8 Claims, 3 Drawing Sheets

DEVICE FOR POSITIONING AND HOLDING A LENGTH OF GAS CHROMATOGRAPHIC COLUMN

This application is a new U.S. utility application claiming benefit of IT MI2005A000980 filed May 26, 2005, the entire contents of which are hereby incorporated by reference.

BACKGROUND OF THE INVENTION

The present invention relates to the field of gas chromatography and particularly relates to a device for positioning and holding one or more lengths of gas chromatographic columns subjected to one or more jets of fluids impinging on one or two spaced apart areas on said column length to change the temperature in this/these area/s.

The device can be particularly applied for the so-called modulation in the comprehensive two dimensional gas chromatography (GC×GC). An example of such a modulator is set forth in the International Application WO 02/39106 in the name of the Applicant, in which two jets of $CO_2$, which are spaced apart from each other and controlled to act in an alternate manner, impinge on two separate areas in a column length being subjected to modulation. Another type of modulator is also known (WO 03/079001 in the name of the Applicant), in which one jet of $CO_2$ impinges on an individual area in the column length. Other exemplary modulators for two dimensional gas chromatography are provided by the International Applications WO 01/51179, with two jets, and WO 03/082427 with an individual jet, both in the name of Zoex.

In any case, there arises the problem of having the gas chromatographic column length, or better, the impingement area/s of the jet/s, in a stable and univocally defined position relative to this/these jet/s, by avoiding any undesired movement of the column length and mainly avoiding vibrations in the column length under the action of the jet/s which may result in damage to the column and/or be detrimental to the effectiveness of modulation.

To solve these problems, according to the prior art, two bushes or ferrules are used, which are fastened to the ends of the column length and are elastically biased away from each other to tension the column length. Normally, for example in the practice of the application WO/023906, one of the two bushes or ferrules is fixed inside the gas chromatographic oven and the other is mounted on a slide which is biased by an adjustable spring in a direction away from the first one. Sometimes, this tensioning is not sufficient to stop the vibrations in the column length and an additional intermediate support is then provided.

This known solution, however, is not completely satisfying, as the column is stressed by the tensioning, the replacement or displacement of the modulation length are very laborious and the response of the tension spring changes over time because of the thermal cycles to which it is inevitably subjected.

Other solutions, which are generally applied with one or more jets focused on an individual spot and with a non-rectilinear column length, provide for a housing plaque in which the capillary column is fixed and arranged in coils, one or more coils thereof protruding from said plaque only in the area subjected to the jets.

This solution, however, does not allow replacing the capillary inside the support.

SUMMARY OF THE INVENTION

In light of the above, it is now an aspect of the present invention to provide a device for the mentioned applications, which eliminates the drawbacks of the known devices, particularly by eliminating the requirement of tensioning the gas chromatographic column length when the modulation is carried out with high flows of cryogenic fluid and to simplify the positioning and replacement of the capillary in the device.

As the column length involved in the modulation is free, the influence of the device on the thermal inertia of said column length is irrelevant to the purposes of modulation.

The device being provided further allows housing two capillaries (columns) with the same or different stationary phase for simultaneous modulation. Said capillaries are arranged in parallel within the device and are both subjected to the same flow or more flows of cryogenic fluid and then simultaneously subjected to the modulation process. Each of them is the second dimension of a two dimensional gas chromatographic columns set, thereby allowing the simultaneous generation of two two-dimensional gas chromatograms.

To achieve these and other objects, the present invention provides a device such as more generally defined in claim 1 and having the details such as described and defined in the dependent claims.

BRIEF DESCRIPTION OF THE DRAWINGS

An exemplary embodiment will be now described in a non-limiting manner, with reference to a dual-jet modulator of the type described in WO 02/39106 and with reference to the annexed figures, in which:

FIG. 3 is a side view of the device in the condition of FIG. 2a.

DETAILED DESCRIPTION OF ILLUSTRATED EMBODIMENTS

Figure 1:
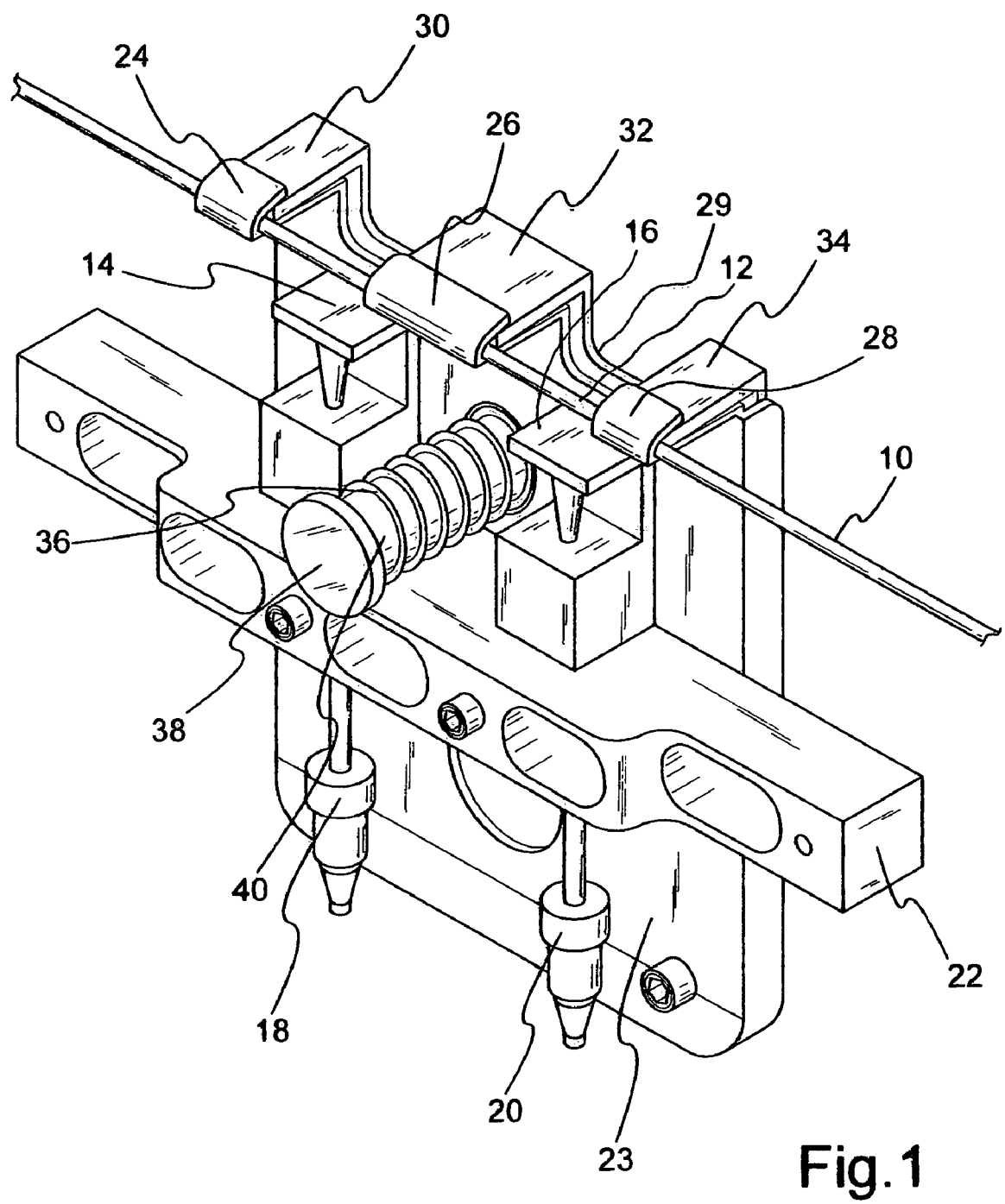
FIG. 1 illustrates a perspective view of a device according to the invention, operably mounted.
Figure 2:
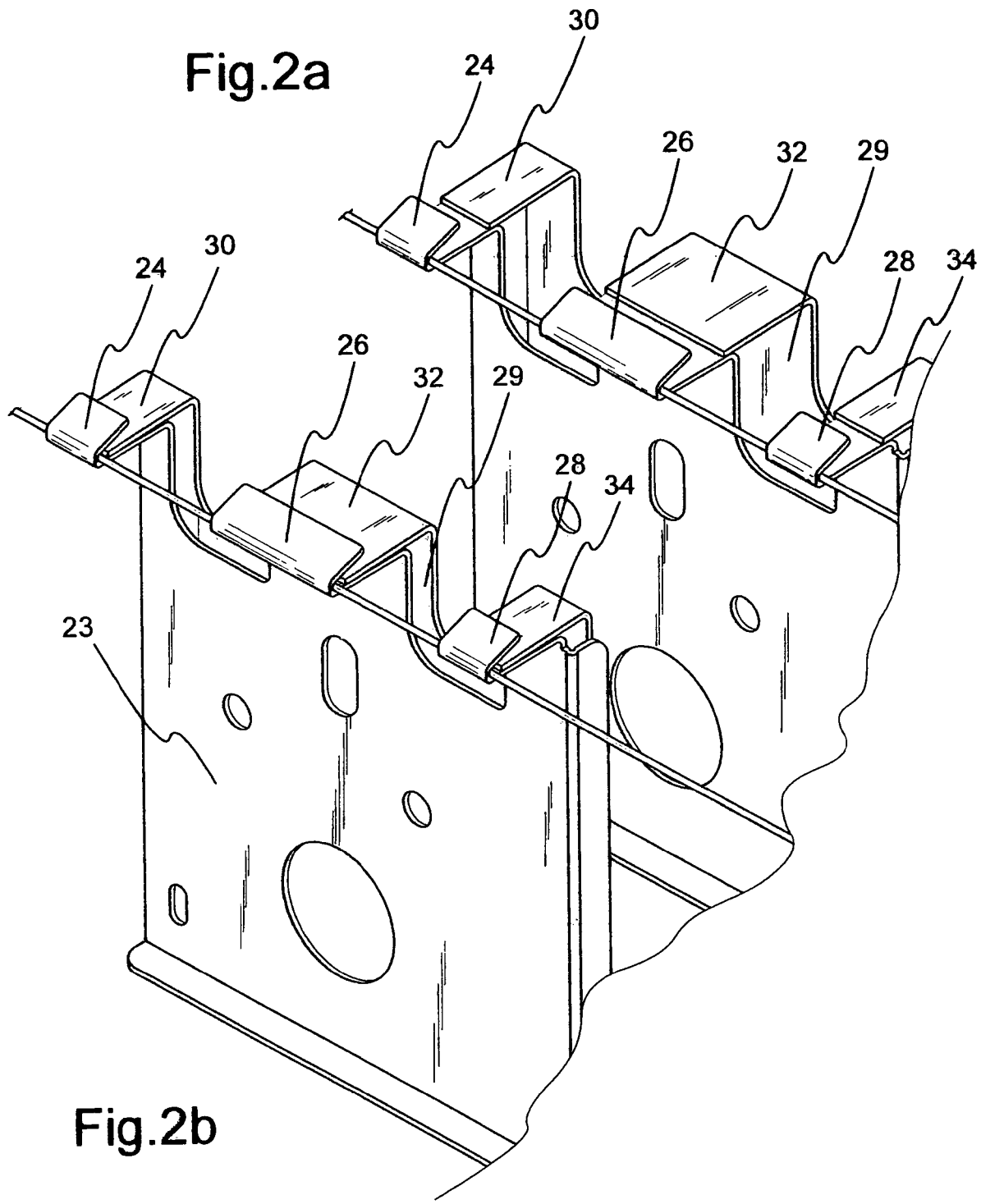
FIGS. 2a and 2b illustrate, still in a perspective view, a part of the device from FIG. 1, in two different positions, open and closed, respectively.
Figure 3:
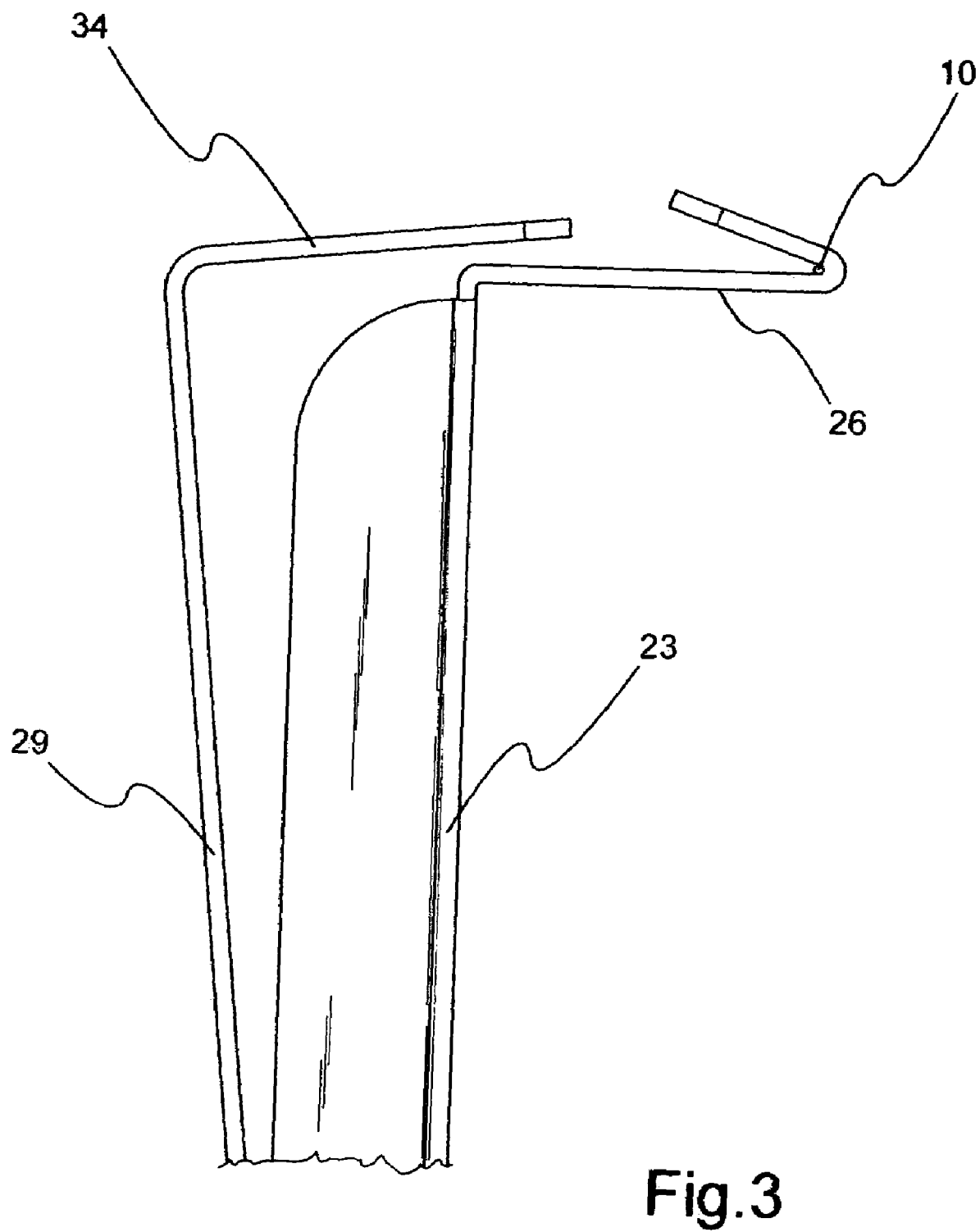

Within an oven for gas chromatography, not shown, there is housed a gas chromatographic column 10, of a known type and consisting of a capillary usually made of fused silica. For comprehensive two-dimensional gas chromatography (GC×GC) applications, the column 10 is formed of two parts, with a length of column 12 subjected to a so-called modulation by means of one or more fluid jets, in the particular case two jets of $CO_2$, impinging on the length 12 and controlled in a pulsed and alternate manner to cool (or heat, when required) one or more areas in this length 12.

The reasons behind the provision of the fluid jets, the operating modes thereof and the performance of the GC×GC analysis are illustrated in the international applications mentioned above, to which reference is made herein.

In the particular case illustrated herein, there are provided two fluid jets 14 and 16 which are fed in a controlled manner through conduits 18 and 20 mounted on a known support block 22 within the gas chromatography oven. The block 22 carries, in any known manner a plate 23, which is fixed relative to the block and ends on top with three shaped appendixes 24, 26 and 28 each defining a V-shaped aperture, the length 12 of column 10 intended for modulation being suitable to be housed and supported in the groove thereof.

The appendixes 24, 26 and 28 extend each in the direction of column 10 by a sufficient length for the column to be supported and positioned in an optimum manner, without however being subjected to important thermal influences due to the jets 14, 16. Furthermore, the position of the appendixes will be such as to allow the column to be freely exposed to the jets 14 and 16 according to the optimal criteria of the GC×GC.

To hold the column in position within the groove of the V-shaped appendixes, a second plate 29 is provided, which is connected to the first one at the opposite end relative to the appendixes 24, 26 and 28, for example by being hinged thereto, to perform an oscillating movement suitable to bring three projections 30, 32 and 34 thereof, which are shaped and sized at the appendixes 24, 26 and 28 within the V-shape of the latter in order to push and hold the column 10 within the groove of the V.

To this purpose, the plate 29 is elastically biased against the plate 23 by an elastic means, such as a compression spring 36 acting against the plate 23 and the button-shaped head 38 of a stem 40 connected to the plate 29 on which the spring 36 is coiled.

By acting on the button 38, the plates 23 and 29 are moved away from each other, the column 10 is positioned within the V-shaped seats and the button 38 is released to hold the spring in position.

The embodiment according to the invention has a very simple structure, it does not stress the column, which is not tensioned, any influence of the thermal cycles on the spring 36 does not influence the positioning mode of the column, and it further allows longitudinally moving the column in a very simple manner to change the modulation length, when required, in addition to allow eliminating the vibrations of the column.

It should be noted that the illustrated arrangement of the column holding means can be advantageously applied when two jets are provided, which act in separate areas in the modulated length 12 of column 10. When an individual jet is provided, two holding means on the sides of the jet will suffice to obtain the same performance and the same advantages.

The invention claimed is:

1. A device for positioning and holding one or more lengths of capillary gas chromatographic column to be subjected to one or more jets of fluid impinging on at least one area of said at least one column length to change the temperature in the at least one area, especially for the modulation of comprehensive two dimensional chromatography (GC×GC), the device comprising at least one support having an open and substantially V-shaped end extending in the direction of the column for housing the column and at least one component suitable to elastically push and hold the capillary column in position within the groove of said V, and which is shaped and sized within the V-shape of said support.

2. A device according to claim 1, wherein the at least one support is provided by a first support element along the foreseen positioning of said column length and the at least one component is provided by a second support element along the foreseen positioning of said column length.

3. A device according to claim 2, further comprising at least biasing device to bias the second support element of the at least one component towards the first support element of the V-shaped supports.

4. A device according to claim 2, wherein the at least one support, the at least one component and said column length are arranged in alignment, such as to allow said column length to be automatically aligned with one or more cryogenic flows.

5. A device according to claim 1, wherein the at least one support and the at least one component are made of metal and their positioning is spaced apart from the area subjected to the one or more jets of fluid to a sufficient extent as to avoid substantial changes in the temperature thereof, which are due to the one or more jets of fluid.

6. A device according to claim 1, further comprising at least two supports and two corresponding components to push and hold said column length, out of the areas involved by the one or more jets of fluid.

7. A device according to claim 6, for modulators using two or more jets of fluid, comprising at least one further support and a corresponding component, which are arranged in a substantially central position between the ends of said column length and out of the areas involved by the one or more jets of fluid.

8. A device according to claim 1, wherein each component includes a plate suitable to penetrate within the V-shape of the support and elastically bias the column into the groove of said V.

* * * * *